(12) United States Patent
Ritzer et al.

(10) Patent No.: US 6,350,893 B1
(45) Date of Patent: Feb. 26, 2002

(54) METHOD FOR THE PRODUCTION OF DIBENZYL CARBONATES

(75) Inventors: Edwin Ritzer, Leverkusen; Claus Dreisbach, Köln, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/673,120

(22) PCT Filed: Apr. 1, 1999

(86) PCT No.: PCT/EP99/02287

§ 371 Date: Oct. 10, 2000

§ 102(e) Date: Oct. 10, 2000

(87) PCT Pub. No.: WO99/52853

PCT Pub. Date: Oct. 21, 1999

(30) Foreign Application Priority Data

Apr. 14, 1998 (DE) .......................................... 198 16 497

(51) Int. Cl.⁷ .............................................. C07C 69/96
(52) U.S. Cl. ...................................................... 558/275
(58) Field of Search .......................................... 558/275

(56) References Cited

U.S. PATENT DOCUMENTS 4,734,119 A  3/1988  Diel et al. ..................... 71/86
4,739,093 A  4/1988  Diel et al. ................... 558/154

FOREIGN PATENT DOCUMENTS

EP  0 106 282  4/1984

OTHER PUBLICATIONS

J. Biol. Chem. 266, Mar. 25, 1991, pp. 5525–5533, Scaman et al, Inhibition of Cytoplasmic Aspartate Aminotransferase from Porcine Heart by R and S Isomers of Aminooxysuccinate and Hydrazinosuccinate.

J. Am. Chem. Soc., 70, Mar. 1948, pp. 1181–1183, Norman Rabjohn, The Synthesis and Reactions of Disazodicarboxylates.

M. Selva et al, Selective mono–benzylation of methylene active compounds with dibenzyl carbonate: benzylation of phenol, J. Chem. Perkin Tran. 1 (month unavailable) 1995, pp. 1889–1893 XP002109750.

*Primary Examiner*—Joseph K. McKane
*Assistant Examiner*—Joseph Murray
(74) *Attorney, Agent, or Firm*—Joseph C. Gil; Diderico van Eyl

(57) ABSTRACT

Dibenzyl carbonates are prepared by reacting a dialkyl carbonate with a benzyl alcohol in the presence of a basic catalyst and removing the highly volatile components and the catalyst from the reaction mixture. This process permits the preparation of benzyl carbonates in a simple manner, in good yields and without any particular technical safety arrangements.

9 Claims, No Drawings

METHOD FOR THE PRODUCTION OF DIBENZYL CARBONATES

FIELD OF THE INVENTION

The present invention relates to a process for preparing dibenzyl carbonates by reacting unsubstituted dialkyl carbonates with optionally substituted benzyl alcohols in the presence of a catalyst.

BACKGROUND OF THE INVENTION

Dibenzyl carbonates are required as precursors for benzyl carbazates. Benzyl carbazates for their part are used as intermediates for preparing crop protection agents and pharmaceutics. In particular, they are used for peptide syntheses (see EP-A 106 282). According to J. Biol. Chem. 266, 5525 (1991), hydrazinosuccinate, an inhibitor of aspartate aminotransferase, can be prepared from benzyl carbazate. EP-A 143 078 describes the use of benzyl carbazate for preparing crop protection agents.

It is known that symmetric dibenzyl carbonates can be prepared by phosgenation (see J. Am. Chem. Soc. 70, 1181 (1948)). This process has the disadvantages that the product is obtained in highly impure form and that the by-product benzyl chloride is always present. Furthermore, this procedure is not particularly economical since the alcohol by-product has to be either disposed of or recovered by an additional isolation step. Finally, the handling of phosgene requires particular technical safety arrangements.

Accordingly, there continues to be a demand for a favourable process for preparing dibenzyl carbonates.

SUMMARY OF THE INVENTION

The present invention, accordingly, provides a process for preparing dibenzyl carbonates of the formula

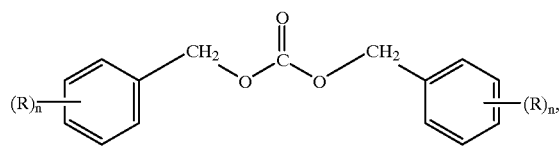

(I)

in which
R in each case represents $C_1$–$C_6$-alkyl, $C_6$–$C_{12}$-aryl or halogen and
n in each case represents zero or an integer from 1 to 5, characterized in that a dialkyl carbonate of the formula

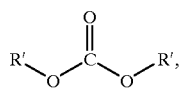

(II)

in which
R' in each case represents a $C_1$–$C_4$-alkyl radical, is reacted with a benzyl alcohol of the formula

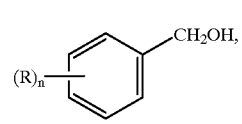

(III)

in which
R and n are as defined under formula (1),
in the presence of a basic catalyst, and the highly volatile components and the catalyst are removed from the reaction mixture.

DESCRIPTION OF THE INVENTION

The two benzyl groups in formula (I) are generally identical. If a plurality of radicals R is present in a benzyl group in the formulae (I) and (III), these can be identical or different.

In the formulae (I) and (III) R preferably represents $C_1$–$C_4$-alkyl, phenyl, fluorine or chlorine and n preferably represents zero, 1 or 2.

Particularly preferably, n represents zero, i.e., according to the invention, particular preference is given to preparing unsubstituted dibenzyl carbonate from a dialkyl carbonate of the formula (II) and unsubstituted benzyl alcohol.

In formula (II) the two radicals R' are generally identical. R' preferably represents methyl or ethyl.

Suitable catalysts for use in the process according to the invention are the most varied basic compounds. For reasons of easier separability, after the process according to the invention has ended, solid basic compounds are preferred for use as catalyst. Examples are: alkali metal hydroxides, such as lithium hydroxide, sodium hydroxide and potassium hydroxide, alkaline earth metal hydroxides, such as calcium hydroxide, alkali metal carbonates and bicarbonates and alkaline earth metal carbonates and bicarbonates, such as lithium carbonate, sodium carbonate, potassium carbonate, calcium carbonate, sodium bicarbonate and potassium bicarbonate, and alkali metal alkoxides or alkaline earth metal alkoxides, such as lithium methoxide and sodium methoxide. When using alkali metal alkoxides and alkaline earth metal alkoxides, preference is given to those which are derived from the benzyl alcohol employed in each case or from the alcohol on which the dialkyl carbonate employed is based (for example, sodium methoxide is preferred if the dialkyl carbonate used is dimethyl carbonate), in order to avoid the formation of undesirable by-products.

It is also possible to use, as catalyst, amino compounds having relatively high molecular weights of, for example, from 100 to 200. Examples of these are bicyclic amino compounds, such as 1,5-diazabicyclo[4.3.0]non-5-ene and 1,8-diazabicyclo-[5.4.0]undec-7-ene. It is also possible to use basic titanium compounds, such as titanium(IV) isopropoxide, and basic tin compounds, such as dibutyltin oxide and dimethyltin didodecanate.

Preferred catalysts are:
sodium carbonate, potassium carbonate, sodium hydroxide and potassium hydroxide The catalyst can be employed, for example, in amounts of from 0.0001 to 20 mol %, based on the dialkyl carbonate used.

For carrying out the process according to the invention, the dialkyl carbonate of the formula (II) in question and the benzyl alcohol of the formula (III) in question and the catalyst can be reacted, for example, in a molar ratio of 1:(20 to 1.6):(0.1 to 0.0001), preferably 1: (8 to 1.8):(0.01 to 0.0003) and particularly preferably 1: (5 to 2):(0.01 to 0.001). If appropriate, the reaction can be carried out in the presence of a solvent which is stable under the reaction conditions, for example in the presence of aromatic hydrocarbons or cycloaliphatic hydrocarbons. The process is preferably carried out in the presence of toluene.

The process according to the invention can, for example, be carried out at temperatures of from 50 to 150° C., preferably from 60 to 160° C., and at a pressure of, for example, from 1 to 0.001 bar.

The alcohol (=R'OH) formed during the course of the process according to the invention is preferably distilled off even during the reaction. This process can be promoted, if appropriate, by addition of an azeotrope former, for example an aromatic hydrocarbon, in particular toluene.

After the reaction according to the invention has ended, the reaction mixture can be worked up, for example, by removing any highly volatile components which may still be present, for example alcohol R'OH, for example by distillation, if appropriate under reduced pressure, and then removing the catalyst, for example by filtration or by extraction with water. Any excess starting material which may be present, for example excess benzyl alcohol of the formula (III), can be removed, if appropriate, by distillation. The reaction product obtainable in this manner can, if appropriate, be purified further with the aid of known methods, for example by (high-vacuum) distillation or (low-temperature) crystallization.

In an exemplary embodiment of the process according to the invention, the starting materials of the formulae (II) and (III) are initially charged together with the catalyst and, if appropriate, a solvent or azeotrope former, the mixture is heated to reaction temperature and the alcohol R'OH formed is removed even during the reaction, for example by distillation, if appropriate under reduced pressure and/or if appropriate together with an azeotrope former. Remaining alcohol R'OH and, if appropriate, any solvent or azeotrope former which is still present can be removed after the reaction has ended, for example at from 100 to 160° C. and with lowering the pressure, for example to down to 0.001 bar. Afterwards, but of course also directly after the reaction has ended, the catalyst can be removed; in the case of a solid catalyst, for example, by filtration or decantation, otherwise, for example, by extraction with water. What remains is the dibenzyl carbonate of the formula (I) prepared, generally in purities of more than 90%, frequently more than 95%.

If this procedure is followed, the last amounts of R'OH removed by distillation generally contain amounts of unreacted dialkyl carbonate of the formula (II). Such fractions can advantageously be added to the next reaction batch.

It is extremely surprising that, using the process according to the invention, it is possible to prepare dibenzyl carbonates of the formula (I) in high purity and in a technically simple manner. The alcohol R'OH, which is formed as by-product in the process according to the invention, can be recycled into the preparation of the dialkyl carbonate of the formula (II) to be used as starting material. The process according to the invention does not require particular technical safety arrangements.

The invention is further described in the following illustrative examples in which all parts and percentages are by weight unless otherwise indicated.

EXAMPLES

Example 1

360 g of dimethyl carbonate, 864 g of benzyl alcohol and 8 g of potassium carbonate were mixed at room temperature and, with stirring at atmospheric pressure, heated to the boil. The methanol formed in this way was distilled off to bring the reaction to completion. During this operation, the bottom temperature increased to up to 140° C. When no more alcohol distilled off, the pressure was reduced more and more, and the bottom temperature was kept constant. When 1 mbar at 140° C. had been reached, these conditions were maintained for 1 hour. The mixture was then cooled to 60° C. and the catalyst was removed by filtration.

Yields:

$1^{st}$ fraction: 328 g of distillate at atmospheric pressure
$2^{nd}$ fraction: 317 g of distillate under reduced pressure
$3^{rd}$ fraction: 473 g of bottom product
GC analysis of the bottom product:
0.48% benzyl alcohol
<1% benzyl methyl carbonate
3.95% dibenzyl ether
91.3% dibenzyl carbonate.

Example 2

Example 1 was repeated; however, only 630 g of benzyl alcohol were used, in addition to the $_2$nd fraction from Example 1.

Yields:

$1^{st}$ fraction: 305 g of distillate under atmospheric pressure
$2^{nd}$ fraction: 116 g of distillate under reduced pressure
$3^{rd}$ fraction: 781 g of bottom product
GC analysis of the bottom product:
1.40% benzyl alcohol
b 3.50% benzyl methyl carbonate
3.56% dibenzyl ether
91.4% dibenzyl carbonate

Examples 3 to 6

Example 1 was repeated, but instead of dimethyl carbonate, diethyl carbonate (DEC) and various catalysts were used. Details are given in Table 1.

TABLE 1

| Ex. No. | DEC (g) | Benzyl alcohol (g) | Catalyst Type | Catalyst (g) | Yield, only bottom product (g) | GC analysis of the bottom product | | | | | |
|---|---|---|---|---|---|---|---|---|---|---|---|
| | | | | | | % I | % II | % III | % IV | Fraction 1 (g) | Fraction 2 (g) |
| 3 | 472 | 864 | $K_2CO_3$ | 8 | 779 | 2.91 | 0.31 | 1.00 | 95.6 | 273 | 187 |
| 4 | 472 | 864 | NaOH | 8 | 597 | 1.06 | 1.24 | 0.06 | 97.5 | 386 | 252 |
| 5 | 472 | 864 | KOH | 8 | 591 | 2.90 | 0.57 | 1.14 | 95.1 | 356 | 287 |
| 6 | 1652 | 3024 | $Na_2CO_3$ | 28 | 2892 | 2.26 | 1.31 | 0.12 | 96.1 | 952 | 596 |

I = Benzyl alcohol
II = Benzyl ethyl carbonate
III = Dibenzyl ether
IV = Dibenzyl carbonate Although the present invention has been described in detail with reference to certain preferred versions thereof, other variations are possible. Therefore, the spirit and scope of the appended claims should not be limited to the description of the versions contained therein.

What is claimed is:

1. A process for preparing dibenzyl carbonates of the formula (I)

(I)

wherein
R represents a $C_1$–$C_6$-alkyl group, a $C_6$–$C_{12}$-aryl group or a halogen, and
n represents zero or an integer from 1 to 5, comprising:
 (A) reacting, in the presence of a basic catalyst,
  (1) a dialkyl carbonate of the formula (II)

in which R' represents a C1–C4-alkyl radical, with
  (2) a benzyl alcohol of the formula (III)

in which R and n are as defined under formula (I); and
 (B) removing highly volatile components and the catalyst from the reaction mixture,
wherein from about 0.0001 to about 20 mol % of a basic catalyst, based on the dialkyl carbonate, is used.

2. The process of claim 1, wherein in the formulae (I) and (III), R represents $C_1$–$C_4$-alkyl, phenyl, fluorine or chlorine and n represents zero, 1 or 2.

3. The process of claim 1, wherein in formula (II), R' represents methyl or ethyl.

4. The process of claim 1, wherein the basic catalyst used comprises a component selected from the group consisting of alkali metal hydroxides, alkaline earth metal hydroxides, alkali metal carbonates, alkali metal bicarbonates, alkaline earth metal carbonates, alkaline metal bicarbonates, alkali metal alkoxides, alkaline earth metal alkoxides, amino compounds having relatively high molecular weights, basic titanium compounds and basic tin compounds.

5. The process of claim 1, wherein the dialkyl carbonate of the formula (II), the benzyl alcohol of the formula (III), and the catalyst are used in a molar ratio of 1: (20 to 1.6):(0.1 to 0.0001).

6. The process of claim 1, wherein the process is carried out in the presence of toluene.

7. The process of claim 1, wherein the process is carried out at a temperature that ranges from about 50 to about 180° C. and at a pressure that ranges from about 1 to about 0.001 bar.

8. The process of claim 1, wherein highly volatile components are removed by distillation.

9. The process of claim 1, wherein the catalyst is removed by filtration or by extraction with water.

* * * * *